United States Patent [19]

Dewhirst

[11] 4,280,842

[45] Jul. 28, 1981

[54] DENTAL-CEMENT COMPOSITION AND METHOD OF PREPARING AND USING SAME

[75] Inventor: Floyd E. Dewhirst, Cambridge, Mass.

[73] Assignee: Forsyth Dental Infirmary for Children, Boston, Mass.

[21] Appl. No.: 21,337

[22] Filed: Mar. 19, 1979

[51] Int. Cl.$^3$ .......................... A61K 6/00; C08K 3/22; C08K 5/07

[52] U.S. Cl. .................................. 106/35; 260/998.11

[58] Field of Search ...... 106/35; 260/439 R, 45.75 R, 260/998.11, 429.9, 591, 439, 429 J

[56] References Cited

U.S. PATENT DOCUMENTS

| | | | |
|---|---|---|---|
| 2,936,242 | 5/1960 | Brauer | 260/429 J |
| 3,361,709 | 1/1968 | Bowen et al. | 260/439 R |
| 3,539,526 | 11/1970 | Bowen | 260/998.11 |
| 4,029,684 | 6/1977 | Avar et al. | 260/45.75 N |
| 4,060,513 | 11/1977 | Molt | 260/45.75 N |

*Primary Examiner*—Allan Lieberman
*Attorney, Agent, or Firm*—Richard P. Crowley

[57] ABSTRACT

A premixed, dental-cement composition, which cement composition comprises a chelate of a metal and hydroxybenzophenone, particularly a zinc hydroxybenzophenone chelate; a filler material, particularly a metal oxide and preferably a metal oxide which is the same as that of the metal hydroxybenzophenone chelate; and a modifier, which dental-cement composition may be heated reversibly between a solid and a liquid state, is premixed and exhibits reduced irritation and solubility over the ordinary dental cements of the prior art.

19 Claims, No Drawings

DENTAL-CEMENT COMPOSITION AND METHOD OF PREPARING AND USING SAME

BACKGROUND OF THE INVENTION

Typical dental-cement compositions now in use comprise polymeric compositions or more particularly comprise the well-known combination of zinc oxide with eugenol or zinc oxide with phosphoric acid. In use, the dentist admixes a liquid component comprising eugenol with other additives and modifiers, together with the powdered zinc oxide and filler material, just before use. The dental-cement composition thereby prepared is then employed typically as a filling material, either temporary or permanent, or for other dental uses. Such prior-art, zinc oxide-eugenol cements and their preparation and uses are set forth, for example, in Skinner's *Science of Dental Materials*, Ralph W. Phillips, Seventh Edition, W. B. Saunders Company, 1973, pages 483–497; "New Developments in Zinc Oxide-Eugenol Cement", *Annals of Dentistry*, Vol. 26 (No. 2), Gerhard M. Brauer, 1967, pages 44–50; and "Improved Zinc Oxide Eugenol Type Cements", *JDR* 41, Gerhard M. Brauer et al, 1962, pages 1096–1102.

A number of other materials have been suggested and tested for use as a dental-cement composition, including zinc phosphate cements, zinc chloride cements and various resins, such as epoxy resins, as well as dental cements which are based on liquid-chelating agents, such as 8-hydroxyquinoline, for example, as more particularly set forth in "The Ability of 39 Liquid Chelating Agents to Form Cements with Metal Oxides, Respecting Their Usability as Root-Filling Materials", T. Halfdan Nielsen, *Acta.Odont.Scand.* 21: 159–174 (1963).

The zinc oxide-eugenol and other zinc oxide bases presently used in dental cements have the distinct disadvantage that they must be admixed by the dentist and be compounded separately just prior to use or application. In addition, such cements vary in solubility and are often irritating to tissue of the patient. It is, therefore, most desirable to provide for an improved dental-cement composition and the preparation and use of such a dental cement which overcomes the disadvantages of the prior art and which provides new and distinct advantages over such prior-art cements, in order to facilitate its easy and rapid use by dentists.

SUMMARY OF THE INVENTION

My invention relates to an improved dental-cement composition and to the preparation and use of such dental-cement composition. In particular, my invention relates to an improved dental-cement composition which is premixed and which is reversibly changed by heat at slightly above body temperature between a liquid and a solid state. More particularly, my improved, premixed, dental-cement composition comprises a eutectic composition of a zinc oxide-hydroxybenzophenone with a filler and modifiers, which premixed composition may be heated reversibly between a solid and a liquid state.

My premixed dental-cement composition is characterized in that the dental-cement composition, on heating to a specified temperature above body temperature; for example, such as a temperature of about 45° C. to 60° C., and particularly about 50° C., changes from a solid to a liquid state, and, on cooling below such specified temperature, changes into a solid state. My premixed dental-cement composition comprises a metal hydroxybenzophenone chelate, or combinations of chelates; a filler material, more particularly a metal oxide and particularly a metal oxide of the metal employed in the chelate, to provide for additional bulk and strength to the solid phase of the chelate; and typically, but optionally, a modifier to improve the working properties of the dental-cement composition.

My premixed dental-cement composition finds use as a dental cement or a temporary or permanent filling material, as a pulp capping agent, as a base under other restorations, as a cement for cast restorations, as an intermediate filling material, as an impression material for dental use, as a periodontal dressing, as a root-canal sealer, as a media for crown and bridge prostheses, as an antiinflammatory dressing of covering for dental tissues, and for other dental or medical uses.

My premixed dental-cement composition provides for significant advantages over the prior-art cements and overcomes many of the problems associated with such prior-art cements, in that my premixed dental-cement composition does not have to be mixed by the dentist just before use, but rather is a premixed composition which the dentist may use merely by heating; for example, in a hydrocolloid bath, to the liquidation temperature of the premixed dental cement, such as, for example, about 50° C. On such heating, the premixed dental cement is liquified and then may be employed in typical fashion by the dentist, either, for example, by the use of a spatula or a syringe. On cooling of my premixed dental cement from the specified temperature, the dental cement solidifies and may be ground, cut, buffed or treated in an ordinary fashion as a typical dental cement. My premixed dental cement is also desirable in that it is less soluble than cements based on zinc oxide and eugenol or zinc oxide and ortho-ethoxybenzoic acid or zinc oxide-phosphoric acid.

Furthermore, the dental cement containing the hydroxybenzophenone is nonirritating to tissue, whereas those cements containing phosphoric acid, eugenol or ortho-ethoxybenzoic acid can be highly irritating to tissues. Ortho-hydroxybenzophenones are potent prostaglandin synthetase inhibitors and possess antiinflammatory activity. Therefore, the dental cement contains O-HB (ortho-hydroxybenzophenones) and has antiinflammatory activities. The dental cement of this invention is premixed and, on heating, reversibly changes between a solid and a liquid state, with a particular temperature adapted to be adjusted to the selection of the type and amount of the chelate employed in the dental composition or admixtures thereof. The dental cement is odorless and tasteless and less soluble than widely used dental cements and possesses good strength and other properties desirable for use as a dental cement.

My dental-cement composition is prepared employing hydroxybenzophenones having the following formula:

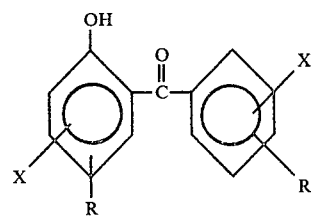
(I)

wherein X represents a halogen, such as chlorine, bromine, fluorine or iodine and preferably chlorine or fluorine; and R represents a hydrogen atom or an alkyl or alkoxy radical preferably of from about 1 to 20 carbon atoms and typically from about $C_1-C_8$, and preferably representing a straight-chain alkyl or alkoxy radical, such as methyl, ethyl, propyl, butyl, methoxy, ethoxy, propoxy, butoxy and similar radicals. Typical 2-hydroxybenzophenones which may be employed in the preparation of my dental composition include, but are not limited to: 2-hydroxybenzophenone; 2-hydroxy-4-methoxybenzophenone; 2-hydroxy-4-octyloxybenzophenone; 2-hydroxy-5-methylbenzophenone; 5-chloro-2-hydroxybenzophenone; 2-hydroxy-4'-chlorobenzophenone; 5-chloro-2-hydroxy-4-methylbenzophenone; 4'-chloro-2-hydroxy-4-methoxybenzophenone; and 2-hydroxy-4-methoxy-4'-methylbenzophenone, and combinations thereof.

The preferred hydroxybenzophenone for my dental cement comprises 4-methoxy-2-hydroxybenzophenone, since it has desirable melting-point and solubility properties. The hydroxybenzophenones may be employed alone or in combination as desired; for example, to raise or lower the particular melting point of the premixed dental composition.

The hydroxybenzophenone metal chelates employed in my dental composition are formed by mixing the selected melted hydroxybenzophenone with a metal oxide, to provide for a fluid mass which sets upon cooling. Where the composition is to be employed as a dental base, the material is admixed to form a putty-like mass, while for use as a cementing agent the viscosity is lower and is highly fluid. The metal oxides which are particularly suitable for use in my dental composition include: zinc oxide, magnesium oxide, calcium oxide, barium oxide, cadmium oxide, mercuric oxide, lead oxide, copper oxide and admixtures thereof, or other divalent metals or metal oxides which form chelates of desirable reversible heating properties. The preferred metal oxide of the invention comprises zinc oxide; although the zinc oxide also may include minor amounts of the other metal oxides. The metal oxides useful in my composition comprise those metals of Group II and the transition metals, particularly the divalent metals.

On admixing the melted hydroxybenzophenone with the metal oxide, a metal hydroxypenzophenone chelate compound is formed which is believed to have the accepted formula as follows:

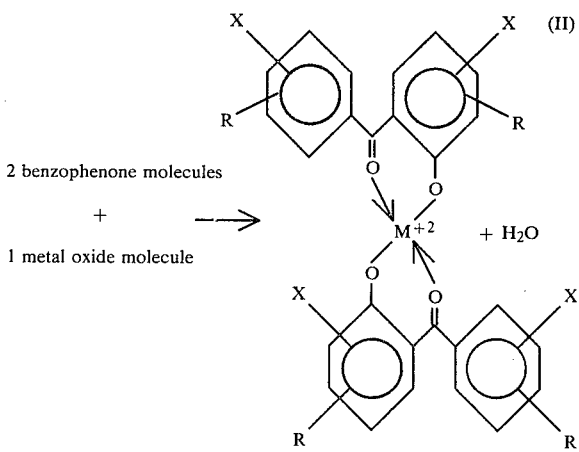

2 benzophenone molecules
+
1 metal oxide molecule wherein X and R are as previously defined in Formula (I); and wherein M represents the divalent metal, particularly a zinc. Metal complexes with hydroxybenzophenones are known and typically have been suggested for use as metal-chelate stabilizers for polyolefin, such as polypropylene (see, for example, U.S. Pat. Nos. 3,296,191; 3,296,239; and 3,361,709, as well as those foreign patents and applications set forth in Chem. Abstracts 82:P171933d; 71:P82165k; 69:P87976m; and 69:P43631y).

As is illustrated, the hydroxybenzophenone forms a 2:1 chelate with the metal, as shown in Formula (II). In my dental-cement composition, typically the metal oxide is in stoichiometric molar excess. The same or a different metal oxide or other filler material may be added, so that the set dental composition comprises the filler material, such as the metal oxide, and preferably the metal oxide of the chelate, embedded in the matrix of the metal hydroxybenzophenone chelate. For example, where the metal oxide benzophenone chelate is formed from the reaction of the zinc oxide and 2-hydroxy-4-methoxybenzophenone, the chelate named zinc, bis-(2-hydroxy-4-methoxybenzophenato) (or, as defined under Chemical Abstracts nomenclature, zinc, bis[(2-hydroxy-4-methoxyphenyl)phenylmethanato-o,o']) is in the dental composition as a matrix, with excess zinc oxide employed as a filler material, to provide additional bulk and strength to the dental composition. The temperature at which the eutectic dental-cement composition changes from a liquid to a solid may be selected by mixing two or more hydroxybenzophenone chelates with different melting points. In some dental compositions, it is, therefore, desirable to provide for more than a single chelate, in order to obtain the desired liquidation temperature. The liquidation temperature may vary; for example, 100° F. to 125° F., but, of course, should be above body temperature, and preferably and typically about 10° above body temperature.

A typical dental-cement composition of my invention is formed merely by mixing the metal oxide and the hydroxybenzophenone, typically with the metal oxide in stoichiometric excess as a filler, and then adding other fillers or modifiers as desired or typically used in dental cements. For example, filler materials employed in the dental-cement composition of my invention may include the metal oxides employed in the chelate or other metal oxides, as well as fused quartz, aluminum oxide, potassium titanate, graphite, aluminum, silver, titanium, stainless steel, silica or other filler materials, such as fibers, such as natural or synthetic fibers; for example, polymeric, asbestos or cotton fibers, or polymers, such as acrylic, epoxy, vinyl-chloride and other polymers employed as polymeric reinforcement agents, and admixtures and combinations thereof.

Such filler materials may range in composition, excluding the chelate, from about 0% to up to 80%, and preferably about 60% to 70%, by weight of the dental composition. The dental composition optionally also may include various modifying agents which aid in the preparation and handling or working properties of the dental cement, which modifiers include those employed in dental compositions, such as rosin or hydrogenated or derivative-type rosins, cottonseed and other types of inert oil, various acids, such as acetic acid, fatty acids and fatty-acid soaps, such as stearates and metal stearates, glycerine and other materials. Modifiers often are employed in varying amounts; for example, in amounts of up to 10%, and typically range from about 1% to 8% of the dental composition, and as high as 50% where the modifier comprises a viscous modifier, such as vaseline, for nonsetting mixtures.

The dental-cement composition may comprise the stoichiometric ratio of the metal oxide with the hydroxybenzophenone, but preferably includes additional metal oxide, so that the dental composition would have a total metal-oxide-to-hydroxybenzophenone weight ratio of up to 8:1, for example, with zinc oxide up to 6:1, and preferably 4:1 to 2:1. The stoichiometric ratio, alone, is not preferred, since such dental cements, comprising only the chelate and without a metal oxide filler material, have low strengths. Therefore, the dental-cement composition, containing a stoichiometric excess of metal oxide, provides high dental strength. It is recognized that the metal oxide provided in excess does not have to be the metal oxide of the particular chelate employed, and a variety of materials may be used as fillers. It is also recognized that the amounts and types of filler materials, modifying agents, chelates or metal oxides may vary as desired, to provide for a dental composition having the particular desirable properties, with the material so admixed so as to provide for a desired liquifaction temperature of the dental cement, so that, on heating above such temperature, the premixed dental composition forms a fluid mass and which, on cooling below the temperature, forms a hard solidified mass.

My invention will be described for the purpose of illustration only in connection with the preparation of certain dental-cement compositions; however, it is recognized that various changes and modifications to such illustrated composition may be made by those persons skilled in the art, without departing from the spirit and scope of my invention.

DESCRIPTION OF THE EMBODIMENTS

An improved, premixed, dental-cement composition of my invention was prepared by mixing zinc oxide and 2-hydroxy-4-methoxybenzophenone at a ratio of approximately 3:1 on a weight-to-weight ratio by melting the hydroxybenzophenone and admixing it with the powdered zinc oxide and incorporating therein an additional filler material of aluminum oxide and a modifying agent of a hydrogenated rosin. A premixed dental cement so prepared had the following composition (w/w): zinc oxide—60%; 2-hydroxy-4-methoxybenzophenone—20%; aluminum oxide—16%; and hydrogenated rosin—4%, for a total of 100%. The above cement was formed by melting the benzophenone and slowly mixing the other constituents into the melted benzophenone. The dental cement so prepared had a liquifaction temperature of approximately 50° C. and, upon cooling below that temperature, set into a hard mass and, when heated above that temperature, formed a heated, fluid mass. The eutectic dental cement so prepared was reversible in that it could be reliquified merely by reheating above the liquifaction temperature.

In use, the dentist merely has to heat the premixed dental composition above its liquifaction temperature and, thereafter, to apply the heated, fluid dental composition as desired. My premixed dental composition may be prepared and used as a premixed composition or prepared and sold in sheets, cubes, rods or other form in amounts, for example, of about 2 to 10 milliliters, with individual use weights ranging from about 2 to 10 grams, or may be prepared in slugs for standard hydrocolloid syringes, or in a disposable aluminum or plastic syringe, so that the syringe containing the premixed material may be heated and the material ejected from the syringe, while in the heated state, by the dentist and then the syringe disposed of after use.

What I claim is:

1. A premixed dental-cement composition adapted for use in the oral cavity of a patient, which dental-cement composition comprises in combination:
   (a) a metal oxide-hydroxybenzophenone chelate compound;
   (b) a dental filler material which comprises a metal oxide in an amount sufficient to provide additional strength to the composition, so that it may be employed as a dental cement;
   said dental-cement composition having a eutectic temperature of from about 100° F. to about 125° F. and characterized by being reversibly changed between a hard solid state, suitable for use as a dental cement, to a liquid state, suitable for application as a dental cement within the eutectic temperature range.

2. The dental-cement composition of claim 1 wherein the metal oxide-hydroxybenzophenone chelate comprises a zinc oxide-hydroxybenzophenone chelate compound.

3. The dental-cement composition of claim 1 wherein the metal oxide-hydroxybenzophenone chelate compound comprises a zinc oxide-2-hydroxy-4-methoxybenzophenone chelate compound.

4. The dental-cement composition of claim 1 wherein the metal of the metal oxide filler material is the same metal oxide as in the chelate compound.

5. The dental-cement composition of claim 1 wherein the dental filler material comprises from about 60% to 70% by weight of the dental-cement composition.

6. The dental-cement composition of claim 1 wherein the hydroxybenzophenone is selected from the group consisting of: 2-hydroxybenzophenone; 2-hydroxy-4-methoxybenzophenone; 2-hydroxy-4-octyloxybenzophenone; 2-hydroxy-5-methylbenzophenone; 5-chloro-2-hydroxybenzophenone; 2-hydroxy-4'-chlorobenzophenone; 5-chloro-2-hydroxy-4-methylbenzophenone; 4'-chloro-2-hydroxy-4-methoxybenzophenone; 2-hydroxy-4-methoxy-4'-methylbenzophenone; and combinations thereof.

7. The dental-cement composition of claim 1 wherein the total weight ratio of the metal oxide to hydroxybenzophenone in the composition ranges up to 6:1.

8. The dental-cement composition of claim 1 wherein the dental filler material comprises zinc oxide, and the total weight ratio of the zinc oxide to hydroxybenzophenone in the composition ranges from about 2:1 to 4:1.

9. The dental-cement composition of claim 1 wherein the metal oxide is zinc oxide, and which dental-cement composition has a eutectic temperature of about 50° C.

10. The dental-cement composition of claim 1 wherein the metal oxide comprises a metal selected from the group consisting of zinc, barium, magnesium calcium, strontium, beryllium, nickel, cobalt, cadmium, mercury, tin and combinations thereof.

11. The dental-cement composition of claim 1 wherein the metal oxide of the chelate compound comprises zinc oxide, and wherein the dental filler material comprises aluminum oxide and zinc oxide.

12. The dental-cement composition of claim 1 which includes a dental composition modifying agent to modify the preparation, handling or working properties of the dental-cement composition.

13. The dental-cement composition of claim 12 wherein the modifying agent includes rosin, glycerine, fatty acids, fatty-acid soaps, petroleum or combinations thereof.

14. A premixed dental-cement composition adapted for use in the oral cavity of a patient, which dental-cement composition comprises in combination:
(a) a zinc oxide-hydroxybenzophenone chelate compound;
(b) a metal oxide dental filler material in an amount sufficient to provide sufficient strength to the dental-cement composition for use as a dental cement;
said dental-cement composition having a eutectic temperature of from about 100° F. to about 125° F. and characterized by being reversibly changed between a hard solid state, suitable for use as a dental cement, to a liquid state, useful for application of the dental cement within the eutectic temperature range.

15. The dental-cement composition of claim 14 wherein the metal oxide dental filler material comprises aluminum oxide and zinc oxide.

16. The dental-cement composition of claim 14 wherein the metal oxide dental filler material includes zinc oxide, the dental-cement composition having a eutectic temperature of about 50° C.

17. The dental-cement composition of claim 14 wherein the total weight ratio of the metal oxide and zinc oxide to hydroxybenzophenone in the composition ranges from about 2:1 to 4:1.

18. The dental-cement composition of claim 17 wherein the hydroxybenzophenone comprises a 2-hydroxy-4-methoxybenzophenone, and wherein the metal oxide dental filler material comprises zinc oxide.

19. The dental-cement composition of claim 14 wherein the hydroxybenzophenone is selected from the group consisting of: 2-hydroxybenzophenone; 2-hydroxy-4-methoxybenzophenone; 2-hydroxy-4-octyloxybenzophenone; 2-hydroxy-5-methylbenzophenone; 5-chloro-2-hydroxybenzophenone; 2-hydroxy-4'-chlorobenzophenone; 5-chloro-2-hydroxy-4-methylbenzophenone; 4'-chloro-2-hydroxy-4-methoxybenzophenone; 2-hydroxy-4-methoxy-4'-methylbenzophenone; and combinations thereof.

* * * * *